(12) United States Patent
Worley et al.

(10) Patent No.: US 6,294,355 B1
(45) Date of Patent: Sep. 25, 2001

(54) SYNAPTIC ACTIVATION PROTEIN COMPOSITIONS AND METHOD

(75) Inventors: Paul F. Worley, Baltimore, MD (US); Paul R. Brakeman, San Francisco, CA (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/042,428

(22) Filed: Mar. 13, 1998

Related U.S. Application Data

(60) Provisional application No. 60/036,553, filed on Mar. 14, 1997.

(51) Int. Cl.$^7$ .................................................. C12N 15/12

(52) U.S. Cl. .................... 435/69.1; 536/23.5; 435/320.1; 435/325; 435/252.3

(58) Field of Search .................... 536/23.5; 435/69.1, 435/320.1, 325, 252.3; 4/6

(56) References Cited

U.S. PATENT DOCUMENTS 5,767,252   6/1998  Worley et al. .

OTHER PUBLICATIONS

Marra et al., Accession No. AA212542, Feb. 19, 1997, Alignment With SEQ ID No. 1.*
Hsu and Perin, "Human Neuronal Pentraxin II (NPTX2): Conservation, Genomic Structure, and Chromosomal Localization,"*Genomics*, 28:220–227 (1995).
Noland, et al., "The Sperm Acrosomal Matrix Contains a Novel Member of the Pentaxin Family of Calium–Dependent Binding Proteins," *J Biol Chem*, 269(51):32607–32614 (1994).
Omeis, et al., "Mouse and Human Neuronal Pentraxin 1 (NPTX1): Conservation, Genomic Structure, and Chromosomal Localization," *Genomics*, 36:543–545 (1996).
Reid and Blobel, "Apexin, an Acrosomal Pentaxin," *J Biol Chem*, 269(51):32615–32620 (1994).
Rudinger, J., "Characteristics of the Amino Acids as Components of a Peptide Hormone Sequence,"*Peptide Hormones*, ed. J.A. Parsons, University Park Press, Baltimore, pp. 1–7 (1976).
Tsui, et al., "Narp, a Novel Member of the Pentraxin Family, Promotes Neurite Outgrowth and Is Dynamically Regulated by Neuronal Activity," *J of Neuroscience*, 16(8):2463–2478 (1996).
Tsui, et al., "Narp, a Novel Member of the Pentraxin Family, Promotes Neurite Outgrowth and Is Dynamically Regulated by Neuronal Activity," *Molecular Biology of the Cell*, 6:214A (1995).
Tsui, et al., "Narp, a Novel Member of the Pentraxin Family of Proteins that is Synthesized, Secreted and Active as a Monomeric Molecule," *Society for Neorscience Abstracts*, 22:299 (1996).

* cited by examiner

*Primary Examiner*—Marianne P. Allen
(74) *Attorney, Agent, or Firm*—Gray Cary Ware Freidenrich; Lisa A. Haile

(57) ABSTRACT

Disclosed are nucleotide coding sequences and polypeptide sequences for synaptic activation binding proteins that are characterized by induction in the central nervous system following neuronal activity in rat hippocampus. Such proteins are identified by (i) substantial homology at the nucleotide or protein sequence level to specifically defined rat, human or mouse coding sequences or proteins, (ii) ability to bind to and affect the activity of effector proteins in the CNS, such as metabotropic glutamate receptors, (iii) binding specificity for a particular binding sequence, and (iv) presence in the sequence of a PDZ-like domain. Nucleotides and polypeptides of the invention are useful in screening and diagnostic assays.

14 Claims, 6 Drawing Sheets

```
ATGGGGGAACAACCTATCTTCAGCACTCGAGCTCATGTCTTCCAGATCGACCCA
AACACAAAGAAGAACTGGGTACCCACCAGCAAGCATGCAGTTACTGTGTCTTAT
TTCTATGACAGCACAAGGAATGTGTATAGGATAATCAGTCTAGACGGCTCAAAG
GCAATAATAAATAGCACCATCACTCCAAACATGACATTTACTAAAACATCTCAA
AAGTTTGGCCAATGGGCTGATAGCCGGGCAAACACTGTTTATGGACTGGGATTCT
CCTCTGAGCATCATCTCTCAAAATTTGCAGAAAAGTTTCAGGAATTTAAAGAAGC
TGCTCGGCTGGCAAAGGAGAAGTCGCAGGAGAAGATGGAACTGACCAGTACCC
CTTCACAGGAATCAGCAGGAGGAGATCTTCAGTCTCCTTTAACACCAGAAAGTA
TCAATGGGACAGATGATGAGAGAACACCCGATGTGACACAGAACTCAGAGCCA
AGGGCTGAGCCAGCTCAGAATGCATTGCCATTTTCACATAGGTACACATTCAATT
CAGCAATCATGATTAAA
```

Fig. 1

| | | | | |
|---|---|---|---|---|
| Homer (rat) | MGEQPIFTTR | AHVFQIDPNT | KKNWMPASKH | 30 |
| Human EST | MGEQPIFTTR | AHVFQIDPNT | KKNWMPASKH | 30 |
| Mouse EST | ---------- | ---------- | ---------- | |
| | | | | |
| Homer (rat) | AVTVSYFYDS | TRNVYRIISL | DGSKAIINST | 60 |
| Human EST | GHRF-YFYDV | TRNSYRIISV | D--------- | 50 |
| Mouse EST | -----YFYDV | TRNSYRIISV | DGAKVIINST | 25 |
| | | | | |
| Homer (rat) | ITPNMTFTKT | SQKFGQWADS | RANTVYGLGF | 90 |
| Human EST | ---------- | ---------- | ---------- | |
| Mouse EST | ITPNMTFTKT | SQKFGQWADS | RANTVFGLGF | 55 |
| | | | | |
| Homer (rat) | SSEHHLSKFA | EKFQEFKERA | RLAKEKSQEK | 120 |
| Human EST | ---------- | ---------- | ---------- | |
| Mouse EST | SSELQLTKFA | EKFQEVRERA | RLARDKSQEK | 85 |
| | | | | |
| Homer (rat) | MELTSTPSQE | SAGGDLQSPL | TPESINGTDD | 150 |
| Human EST | ---------- | ---------- | ---------- | |
| Mouse EST | TETSSNHSQE | S-GCETPSST | QASSVNGTDD | 114 |
| | | | | |
| Homer (rat) | ERTPDVTQNS | EPRAEPAQNA | LPFSHRYTFN | 150 |
| Human EST | ---------- | ---------- | ---------- | |
| Mouse EST | EKASHASPAD | THLKSENDKL | KIALTQSAAN | 144 |
| | | | | |
| Homer (rat) | SAIMIK.-- | | | 186 |
| Human EST | --------- | | | |
| Mouse EST | VKKWEMELQ | | | 153 |

Fig. 2

Fig. 9A  mGluR1α  -  RDYKQSSSTL
Fig. 9B  mGluR2  -  EVVDSTTSSL
Fig. 9C  mGluR3  -  EVLDSTTSSL
Fig. 9D  mGluR4  -  TYVTYTNHAI
Fig. 9E  mGluR5  -  RDYTQSSSSL
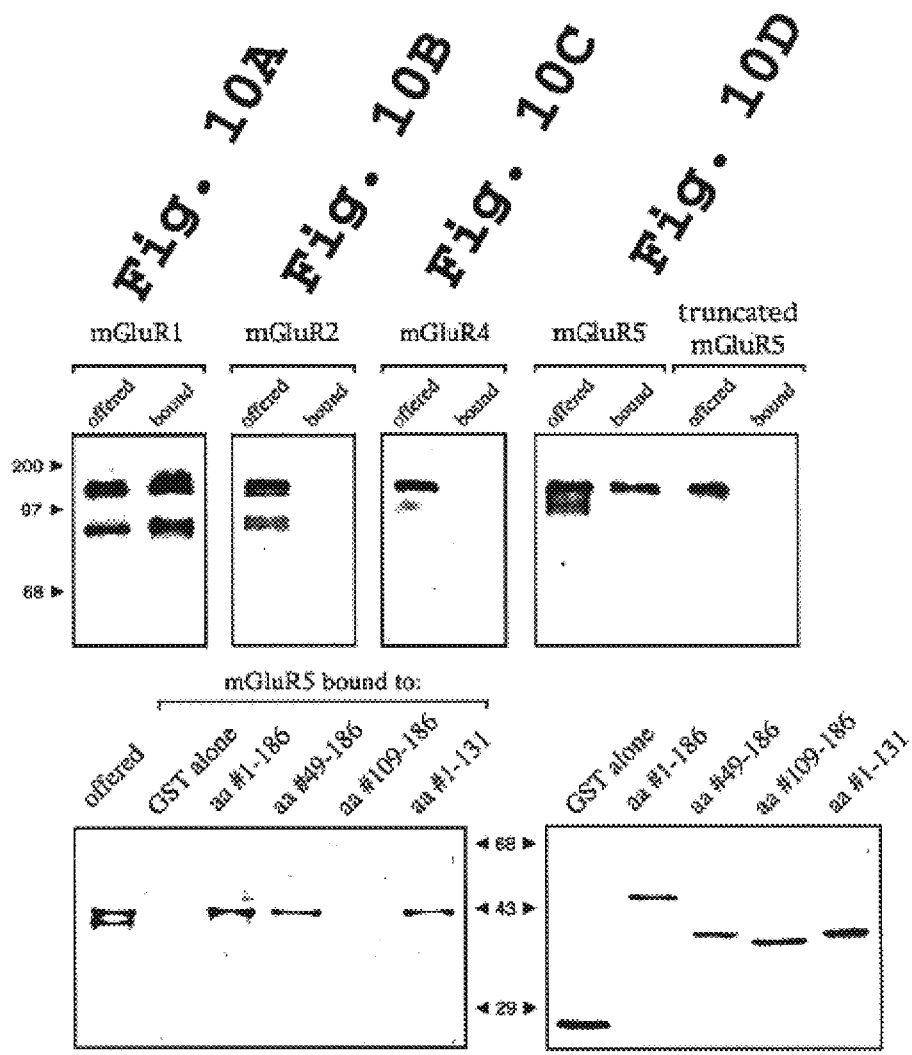

Fig. 11
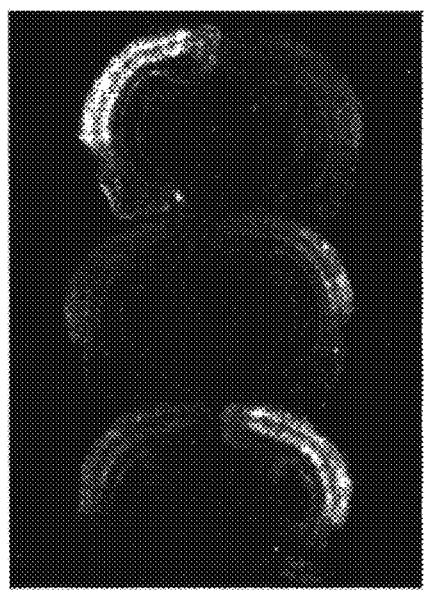
Fig. 12A  Fig. 12B
Fig. 12C  Fig. 12D
Fig. 12E  Fig. 12F
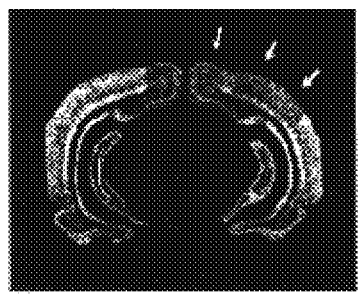
Fig. 13
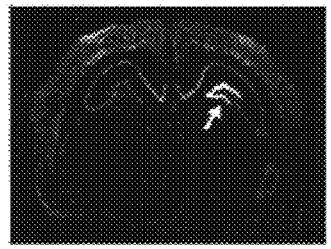
Fig. 14
Fig. 15

SYNAPTIC ACTIVATION PROTEIN COMPOSITIONS AND METHOD

This application claims the priority of U.S. Provisional Application No. 60/036,553, filed Mar. 14, 1997, which is pending as of the filing date of the present application, and which is incorporated herein by reference.

This invention was made with United States Government support by Grant No. K02MHO1152-O1A2 from the National Institutes of Mental Health and Grant No. RO1DA10309-01 from NIDA. The United States Government therefore has certain rights in this invention.

FIELD OF THE INVENTION

The present invention is concerned with a new family of synaptically activated proteins, and in particular, a protein that specifically binds to and alters the function of metabotropic glutamate receptors.

REFERENCES

Ausubel, F. M., et al., in CURRENT PROTOCOLS IN MOLECULAR BIOLOGY, John Wiley and Sons, Inc., Media Pa. (1992).

Chevray, P. M., and Nathans, D., Proc. Natl. Acad. Sci. USA 89:5789–5792 (1992).

Dayhoff, M. O., in ATLAS OF PROTEIN SEQUENCE AND STRUCTURE Vol. 5, National Biomedical Research Foundation, pp. 101–110, and Supplement 2 to this volume, pp. 1–10 (1972).

Doyle, D. A., et al., Cell 85:1067–1076 (1996).

Garvey, J. S., et al., in METHODS IN IMMUNOLOGY, Benjamin Cummings, Reading, Mass. (1977).

Howard, G. C., Ed., METHODS IN NONRADIOACTIVE DETECTION, Appleton & Lange, Norwalk, Conn. (1993).

Kornau, H. C., et al., Science 269:1737–1740 (1995).

Nakanishi, S., Neuron 13:1031–7 (1994).

Pin, J. P., and Duvoisin, R., Neuropharmacology 34:1–26 (1995).

Sambrook, et al., MOLECULAR CLONING: A LABORATORY MANUAL (Second Edition) Cold Spring Harbor, N.Y. (1989).

BACKGROUND OF THE INVENTION

Spatial localization and clustering of membrane proteins is critical to neuronal development and synaptic plasticity. Proteins that interact with plasma membrane proteins are thought to affect the spatial distribution of such membrane proteins. These interactions are may be important in regulating the function(s) of membrane proteins, such as neurotransmitter receptors, which control synaptic activity in the central nervous system.

The present invention concerns the discovery of a new family of proteins that are enriched in the mammalian central nervous system and that interact with proteins involved in synaptic function. These proteins are involved in synaptic function, as evidenced by their induction by neuronal activation, such as seizures, visual stimulation, acute cocaine, trauma, and the like. These proteins are collectively termed "synaptic activation proteins."

A novel dendritic protein, termed "Homer", exemplifies the present invention. This protein contains a single, PDZ-like binding domain and binds specifically to the C-termiinus of metabotropic glutamate receptors. Metabotropic glutamate receptors release intracellular calcium by activating phospholipase C, which catalyzes the hydrolysis of membrane phosphoinositides. However, other than containing a PDZ-like domain, the Homer protein does not otherwise resemble known PDZ proteins and has less than 10% sequence identity with the closest PDZ protein. Additionally, the Homer protein is regulated as an immediate early gene. This dynamic transcriptional control suggests that Homer mediates a novel cellular mechanism to regulate metabotropic glutamate signaling.

The features outlined for the Homer protein characterize a novel family of proteins, synaptic activation proteins, which form the basis for the present invention. Because these proteins are involved in synaptic function, they have particular utilities, for example, in screening assays for drugs that affect synaptic function and are therefore centrally active, as further described below.

SUMMARY OF THE INVENTION

The present invention is concerned with a novel family of proteins that are present in the mammalian central nervous system. These proteins are particularly characterized by (i) their enhanced expression in mammalian central nervous tissue in response to synaptic activation, and (ii) a novel PDZ-like binding domain.

The new protein family is exemplified by a rat protein, termed "Homer" (SEQ ID NO: 2). Other members of the family have a sequence that is substantially identical (e.g., at least 70% or greater sequence identity, and preferably 80% or greater sequence identity) to that of the rat protein, or to the human and mouse members of the family, setments of which are shown herein as SEQ ID NO: 3 and SEQ ID NO: 4. The full length versions of these latter peptides, insofar as they are revealed by the discovery of the full-length sequences described herein, also form part of the present invention. The present invention also include species homologs and/or compositions based on internally consistent variations between SEQ ID NO: 2 and such full length species homologs, as described herein.

More specifically, proteins having sequences that comprise internally consistent variants among the disclosed sequences, including conservative amino acid substitutions thereof, also form a part of the invention. Family members may be identified by low stringency hybridization, degenerate PCR, or other methods that detect nucleotide or amino acid sequences that are at least about 70%, and in a preferred embodiment at least 80%, identical to SEQ ID NO: 1 or SEQ ID NO: 2, respectively.

Proteins of the invention are particularly useful for use in screening assays for centrally active drugs. The proteins are also useful components of diagnostic assays for measuring induction of synaptic activation, as may occur in response to multiple stimuli that result in synaptic activation. Similarly, peptide fragments from such proteins, particularly peptide fragments derived from the binding site between such proteins and their synaptic effector binding partners, have utility as inhibitors long term consequences of abnormal synaptic activation.

In a related embodiment, the invention includes polypeptides as described above, but which further exhibit an ability to selectively bind to a synaptic membrane protein having a C-terminal peptide region selected from the group consisting of SSSL and SSTL.

In a related aspect, the invention also includes nucleotide sequences that encode members of the novel protein family described herein. Accordingly, nucleotide sequences having substantial identity to the disclosed Homer protein coding sequences (such as SEQ ID NO: 1), as well as the disclosed sequences themselves, are also included within the invention.

Also forming a part of the invention are vectors containing the polynucleotide sequences described above. Such vectors are useful, for example, in the production of the claimed proteins by recombinant techniques.

In a related aspect, the invention also includes a method of selecting a compound that interferes with binding of a synaptic activation protein to a cellular binding protein in the mammalian central nervous system. The method includes adding a test compound to a reaction mixture containing (i) an isolated synaptic activation protein having substantial identity to one or more of the polypeptides having the substantial sequence identity to the polypeptide having a sequence presented as SEQ ID NO: 2, (ii) an isolated binding protein to which the synaptic activation protein binds, and (iii) means for detecting binding between the synaptic activation protein and said binding protein. Binding of the binding protein to the synaptic activation protein is measured in the presence of a test compound and compared to binding measured in the absence of the test compound. A test compound is selected for use as a centrally active drug if such comparison reveals a substantial difference in binding under these conditions.

In a particular embodiment, the binding protein in the assay method is a metabotropic glutamate receptor polypeptide which includes a sequence selected from the group consisting of SSSL and SSTL. In another particular embodiment, the binding protein is an mGluR linked to phosphoinositidase C. In yet another embodiment, mGluR is expressed in cells, and binding between the receptor and the binding protein is measured by measuring phosphoinositidase C activity in cells.

These and other objects and features of the invention will become more fully apparent when the following detailed description of the invention is read in conjunction with the accompanying drawings.

BRIEF DESCRIPTION OF THE FIGURES

FIG. 1 shows the open reading frame nucleotide coding sequence (ORF) of a synaptic activation protein derived from rat (SEQ ID NO: 1);

FIG. 2 shows the deduced amino sequence of rat ("Homer"; SEQ ID NO: 2), and compares amino acid sequences derived from EST's of human (SEQ ID NO: 3) and mouse (SEQ ID NO: 4) synaptic activation proteins;

FIGS. 9(A–E) shows the C-terminal ten amino acids of metabotropic glutamate receptors mGluR1α (9A), mGluR2 (9B; SEQ ID NO: 6), mGluR3 (9C; SEQ ID NO: 7), mGluR4 (9D; SEQ ID NO: 8), and mGluR5 (9E; SEQ ID NO: 9);

FIGS. 10A–10D show computer-generated images of an immunoblot analysis of in vitro binding by the Homer protein of metabotropic glutamate receptors mGluR1 (10A), mGluR2 (10B), mGluR3 (10C), mGluR5 and truncated mGluR5 (10D) to Homer protein, demonstrating selective binding of Homer protein to mGluR1α and mGluR5;

FIGS. 10E–10F show results of immunoblot analysis of in vitro binding assays used to examine deletion constructs of GST-Homer for binding to myc-tagged mGluR5 C-terminus (195 aa) expressed in HEK-293 cells, where lane markers indicate the portion of Homer expressed, where immunoblot shown in FIG. 10E was immunoblotted for myc and demonstrates mGluR5 binding to full length Homer (1–186) and fragment 1–131 but not to fragment 109–186, and where image shown in FIG. 10F is Comassie stain of Homer deletion constructs;

FIG. 11 shows a computer-generated image of a Northern blot (10 µg total RNA) showing postnatal increase in Homer mRNA in rat forebrain;

FIGS. 12(A–F) show a computer-generated images of coronal sections taken from dark-reared rat pups sacrificed in the dark (12B, 12C) or exposed to ambient room light for 30 minutes prior to sacrifice (12A, 12F) compared to age matched control rats raised in normal diurnal conditions (12D, 12E) and subjected to in situ hybridization with a radiolabeled antisense RNA probe specific for the 3' non-translated region of Homer;

FIG. 13 shows a computer-generated image of an in situ hybridization experiment demonstrating the effect of a uniocular injection of tetrodotoxin (TTX) into the eye of rats prior to sacrifice;

FIG. 14 shows a computer-generated image showing an in situ hybridization experiment demonstrating induction of Homer mRNA in association with long term potentiation (LTP), where arrow indicates induced expression of Homer RNA in hippocampal granule cells following a synaptic stimulus that produced LTP; and FIG. 15 shows a computer-generated image showing an in situ hybridization experiment demonstrating induction in the striatum of Homer by administration of cocaine (10 mg/kg) intraperitoneally 2 hours prior to sacrifice.

DETAILED DESCRIPTION OF THE INVENTION

I. Definitions

Figure 3:
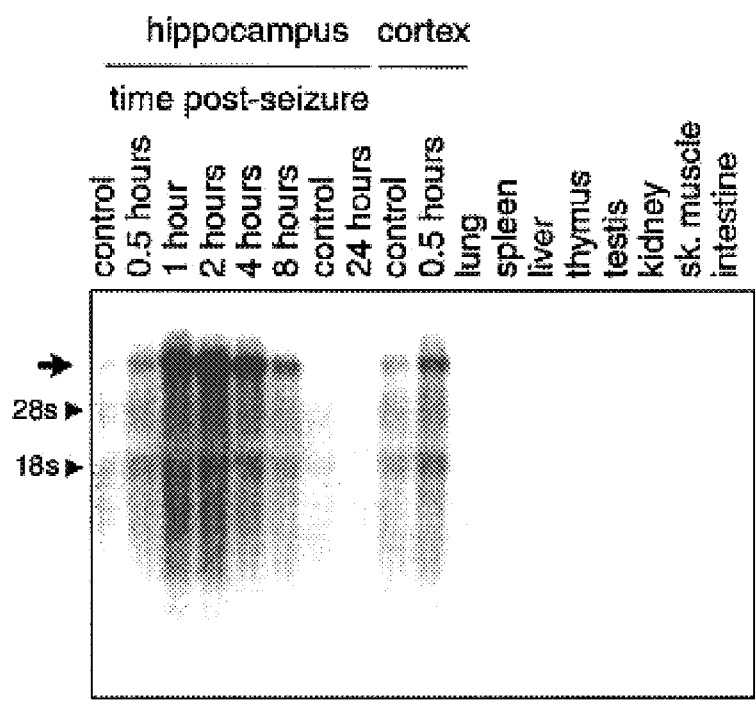
FIG. 3 shows a computer-generated image of a Northern blot of total RNA (10 µg) from rat brain (hippocampus, cortex) and other indicated organs, showing rapid and transient induction by seizures of the 6.5 kb (approx.) mGluR binding protein in the hippocampus and cortex.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

The term "vector" refers to a nucleotide sequence that can assimilate new nucleic acids, and propagate those new sequences in an appropriate host. Vectors include, but are not limited to recombinant plasmids and viruses. The vector (e.g., plasmid or recombinant virus) comprising the nucleic acid of the invention can be in a carrier, for example, a plasmid complexed to protein, a plasmid complexed with lipid-based nucleic acid transduction systems, or other non-viral carrier systems.

The term "polypeptide" as used herein refers to a compound made up of a single chain of amino acid residues linked by peptide bonds. The term "protein" may be synonymous with the term "polypeptide" or may refer, in addition, to a complex of two or more polypeptides.

As used herein, the terms "substantial homology" or "substantial identity", and declinations thereof, refer to concordance of an amino acid sequence with another amino acid sequence or of a polynucleotide sequence with another polynucleotide sequence of at least 70% or preferably, at least 80%, when such sequences are arranged in a best fit alignment. In the case of nucleotide sequences, the terms also imply that the nucleotide sequence in question is capable of being detected in a screening assay by a hybridization probe derived from the nucleotide sequence defined as SEQ ID NO: 1 (Homer coding sequence) under moderate stringency conditions. (Ausubel)

An "alignment" refers to the arrangement of two or more amino acid or nucleic acid sequences in such a way as to align areas of the sequences sharing common properties. The degree of relatedness or homology between the sequences is predicted computationally or statistically based on weights assigned to the elements aligned between the sequences.

Percent (%) identity, with respect to two amino acid sequences, refers to the percent of residues that are identical in the two sequences when the sequences are optimally aligned. Optimal alignment is defined as the alignment giving the highest percent identity score. Such alignments can be performed using the "GENEWORKS" program. Alternatively, alignments may be performed using the local alignment program LALIGN with a ktup of 1, default parameters and the default PAM. In the context of the present invention, when it is stated that a protein or nucleic acid has 80% identity to a given sequence, it is implicit that this refers to the entire sequence of the longer of the two proteins. Thus, for example the deduced translation product of an EST that is identical to the full length sequence SEQ ID NO: 2 for the length of the EST product, but where the EST product is only 25% of the length of the full length sequence, is not considered to fall within a claimed sequence defined as having 80% or more sequence identity to SEQ ID NO: 2.

The term "PDZ-like" binding domain refers to a portion of a polypeptide that contains one or more repeats of the amino acid GLGF and, preferably, a preceding basic amino acid, such as an arginine, preferably, separated from GLGF by 1–10 residues.

As used herein, the term "metabotropic glutamate receptor" or "mGluR" refers to a glutamate binding site which is functionally linked to either adenylate cyclase (AC) or phosphoinositidase c (PI-PLC). At least five neuronal metabotropic glutamate receptors have been identified: mGluR1 and mGluR5 are linked to PLC; mGluR2 and mGluR4 regulate AC activity.

As used herein, the term "metabotropic glutamate receptor binding protein" refers to a polypeptide that binds to one or more metabotropic glutamate receptors, as evidenced by co-immunoprecipitation of the binding protein and mGluR by an anti-mGluR antibody, or by in vitro binding as compared to a non-relevant control protein. A typical binding affinity for this interaction is at least about $10^{-6}$ M.

The term "central nervous system" (CNS) refers to the brain and spinal cord, including the cerebrospinal fluid (CSF).

The term "splice variant" refers to a protein that is coded by a common gene but which has a sequence that is altered due to alternative splicing of the mRNA prior to translation.

An "expressed sequence tag" or EST is a short (typically 200–300) bp segment derived from a cDNA sequence, whose sequence is unique, as evidenced by ability to be selectively amplified using specific primers in a polymerase chain reaction. ESTs generally do not represent full length sequences.

Amino acid residues are referred to herein by their standard single letter notations: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; X, hydroxyproline; Y, tyrosine.

II. Isolation of Binding Proteins

It is the discovery of the present invention that activation of excitatory synaptic activity in brain results in enhanced expression of a novel family of proteins, referred to herein as "synaptic activation proteins", and exemplified by a rat protein referred to herein as "Homer". Together with its splice variants and its homologues from other species, this protein defines the new family of synaptic activation proteins that bind to and affect the activity of certain physiological effectors (e.g., receptors, ion channels, transport proteins, enzymes) in the central nervous system.

1. Isolation of Nucleotide Coding Sequences for Synaptic Activation Proteins a. Identification of Coding Sequence By way of example, the rat protein referred to herein as the rat Homer protein was initially identified by differential screening on the basis of its rapid induction of expression during excitatory synaptic activity in the hippocampus and cortex. Additional synaptic activation proteins can be identified by this method or by the homology screening methods described in Section 2, below.

Example 1 provides details of the differential screening method used to identify the rat Homer protein. Briefly, Poly(A)$^+$RNA was extracted from brains of animals having active seizures and was used to make cDNA. This stimulated cDNA was hybridized to excess RNA from the brains of non-stimulated control animals. cDNA made from the subtracted mRNA was then used to construct a library, from which the rat Homer protein was identified. As discussed herein, this protein has particular sequence characteristics and binding properties that define a family of synaptic binding or activation proteins.

In a differential screening procedure, a total of 16 novel, independent clones were identified that appeared to have higher levels in the stimulated than control rat hippocampus. Differential mRNA expression was confirmed by standard Northern analysis. The rat Homer protein was produced as a translation product of one of these differentially expressed clones. Northern analysis demonstrated that Homer mRNA is ~6.5 kB in length. Several full length cDNAs of the rat Homer protein were identified by screening a phage library (λ Zap II) that was specially prepared to contain large cDNAs. Both strands of two independent clones were sequenced and a 558 nucleotide open reading frame (ORF) was identified. The ORF was confirmed by analysis of the size of the protein product generated by in vitro transcription and translation of in vitro mRNA prepared from the putative full length clones and comparing this with protein prepared with mRNA from clones that lacked the start methionine. The ORF was additionally confirmed by preparing rabbit polyclonal antisera against either a bacterial fusion protein of full length Homer or against a synthetic peptide representing the C-terminus of the Homer protein. These antisera were used to confirm the presence of an appropriately sized protein in brain that is rapidly induced following maximal electroconvulsive seizures (MECS).

The nucleotide coding sequence of the Homer protein isolated from rat brain is shown in FIG. 1 as SEQ ID NO: 1. The coding sequence has an open reading frame (ORF) of 558 nucleotides (FIG. 1A; SEQ ID NO: 1). As mentioned above, a 6.5 kb mRNA derived from this DNA encodes a 186 amino acid protein (FIG. 2A; SEQ ID NO: 2). A long 3' UTR (GENBANK accession #: U92079) encodes multiple AUUUA repeats, such as have been implicated in mRNA destabilization of immediate early genes (IEG). The amino acid sequence predicts a soluble protein that contains a single GLGF sequence and a preceding arginine (FIG. 2), a so-called "PDZ-like domain" which is predicted to have certain binding properties, based on its characterization in different, unrelated proteins, such as PSD-95. The Homer protein sequence is otherwise novel and unpredictable from shorter sequences such as ESTs. There is less than 10% amino acid sequence identity between rat Homer and reported members of the PDZ family (Doyle, et al., 1996).

Expressed sequence tags (ESTs) from human (Z17805) and mouse (AA166092 and AA013888) were identified that are 84% and 72% identical to regions of the ORF coding sequences for Homer protein (FIG. 2; human, SEQ ID NO: 3 and mouse, SEQ ID NO: 4). Translation of the ESTs indicates that the amino acid sequences of the mouse and human ESTs are identical to each other in their limited region of overlap but the mouse ESTs are divergent from the rat Homer protein in this region, suggesting that the ESTs are homologues of additional family members. On the basis of the present discovery of rat Homer, the human and mouse protein sequences can be extended to include the rat sequence and/or conservative substitutions thereof, as described herein. Such extended sequences will fall within the definition of a synaptic activation protein family member, as defined herein.

Additional synaptic activation protein family members can be identified using a differential screening protocol similar to that described in Example 1, in conjunction with probes based on the sequences described herein, according to methods known in the art. Alternatively or in addition, such proteins are identified by (i) substantial homology at the nucleotide or protein sequence level to the rat Homer coding sequence or protein, (ii) ability to bind to and affect the activity of effector proteins in the CNS, such as metabotropic glutamate receptors, (iii) binding specificity for a particular binding sequence, and (iv) presence in the sequence of a Homer PDZ-like domain. As implied by its differential expression in stimulated rat brain, as discussed above, and as described further below, expression of the gene is stimulated by excitatory synaptic activity. These attributes of synaptic activation proteins are described in the sections that follow.

b. Identification of Synaptic Activation Protein Homologs

From the present disclosure of the rat Homer coding and polypeptide sequences, identification of additional members of the Homer polypeptide family having substantial homology to Homer can be accomplished by one or more methods known to persons skilled in the art, and discussed below.

For example, using nucleotide probes derived from SEQ ID NO: 1, the family members are identified by screening appropriate libraries. In particular, hybridization probes derived from nt 558-nt 1127 of the nearly full length cDNA reported to Genbank (Accession #: U92079) can be synthesized on commercially available DNA synthesizers (e.g., Applied Biosystems Model 381A) using standard techniques well known in the art (Ausubel, et al., 1992). A particularly appropriate library is a CNS or brain library, such as the human brain libraries which are commercially available from Stratagene (La Jolla, Calif.) and InVitrogen (San Diego, Calif.). The probe is typically hybridized at 65° C. and washed at 55° C. (moderate stringency screens). Clones identified by this method are isolated and their coding sequences determined, according to methods known in the art. Clones are further selected if their deduced amino acid sequences minimally include a Homer PDZ-like domain region, as discussed above.

Further characterization of selected clones is carried out by insertion of the isolated coding regions into vectors for expression in an appropriate expression system, such as any one or more of the systems described in Example 3, or in other appropriate systems known in the art. Translated products are then isolated, such as by the methods described in Example 4, and are tested for ability to bind to specific target proteins in the CNS and binding specificity for a particular peptide binding sequence, such as the sequence SSTL or SSSL, as discussed in Section III.C., below.

Further, using the protein sequences presented as SEQ ID NO: 2 (rat Homer), SEQ ID NO: 3 and SEQ ID NO: 4, shown in FIGS. 2(A–C), as templates, it is appreciated that additional family members can be identified based on (i) sequence variation between and among the polypeptides and (ii) conservative substitution of amino acids within the sequences.

Thus, looking at the N-terminal region of the polypeptides shown in FIG. 2, it is apparent that the first 30 amino acids are invariant among the three sequences. However, positions 31–34 differ. The rat sequence is AVTV, while the human and mouse proteins share the sequence GHRF. From this variation, it is possible to construct polypeptides in which positions 31–34 have the variable sequences: A/G V/H T/R V/F. Further regions of variability are apparent from inspection of the aligned sequences. Certain regions of the rat Homer protein have been identified as significant in the context of its function. For example, the PDZ-like domain GLGF sequence and preceding arginine at positions 87–90 and 81, respectively, may form a "binding pocket", based on the known binding pocket of the synaptic binding protein PSD95 (Kornau, et al., 1995). In accordance with the foregoing guidelines concerning substitution, this region is invariant among the three exemplified synaptic activation proteins and should therefore be conserved in any sequences deduced from these proteins.

Further substitution at the identified variable positions may be made by making conservative amino acid substitutions. That is, if the two or more of the possible amino acids at a variant position are in a common substitution class, substitution at that position by an amino acid within that class may preserve the conformation and function of the polypeptide. Standard substitution classes that can be used in this analysis are the six classes based on common side chain properties and highest frequency of substitution in homologous proteins in nature, as determined, for example, by a standard Dayhoff frequency exchange matrix (Dayhoff, 1972). These classes are Class I: C; Class II: S, T, P, X A, and G representing small aliphatic side chains and OH-group side chains; Class III: N, Q, D, and C, representing neutral and negatively charged side chains capable of forming hydrogen bonds; Class IV: H, R, and K, representing basic polar side chains; Class V: I, V, and L, representing branched aliphatic side chains, and Met; and Class VI: F, Y, and W, representing aromatic side chains. In addition, each group may include related amino acid analogs, such as ornithine, homoarginine, N-methyl lysine, dimethyl lysine, or trimethyl lysine in class IV, and cyclohexylalanine or a halogenated tyrosine in Group VI. Further, the classes may include both L and D stereoisomers, although L-amino acids are preferred for substitutions.

Polypeptide sequences designed according to the foregoing guidelines can be produced, for example by recombinant expression. The selected ORF is cloned as a fusion with glutathionione-S-transferase (GST) and is express in bacteria. Alternatively, the ORF may be cloned into a mammalian expression vector and expressed in mammalian cells, according to methods known in the art.

c. Preparation of Synaptic Activation Protein Oligonucleotides/Vectors

Based on the protein sequences revealed through the foregoing analysis, nucleotides encoding synaptic activation proteins can be designed, according to methods known in the art. As discussed below, such design may include considerations of the type of cells used for expression of the protein.

The nucleotide sequences of the present invention can be engineered in order to alter the protein coding sequence for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns, to change codon preference, to produce splice variants, etc.

The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., 1989.

As detailed in Example 2, a mammalian expression construct of the full length rat Homer protein was prepared by cloning the 5' EcoRI fragment (1.6 kb) into the mammalian expression vector pRK5. The vector was used to transfect mammalian eukaryotic cells (human embryonic kidney; HEV-293 cells).

Alternate vectors may be used for transfection of different cell types. For example, for expression of a fusion protein containing the rat Homer polypeptide fused to GST, the Homer ORF was cloned into the bacterial vectors pGEX. For expression in a yeast system, the Homer ORF was cloned into pPC86.

2. Production of Synaptic Activation Proteins a. Expression of Synaptic Activation Proteins Synaptic activation proteins may be produced recombinantly by any of a number of methods available for expression of proteins. By way of example, Example 3 provides methods that have been used to express the rat Homer protein in a cell-free transcription/translation system.

For larger scale production, expression of the Homer protein and synaptic activation protein family member homologues can be carried out in any of a number of cellular expression systems. Possible host cells include but are not restricted to bacterial, yeast, insect, and mammalian cells. It is appreciated that expression in a particular system may be optimized by tailoring codons to the particular cell type in which expression is to occur. Hence polynucleotides encompassed by the present invention shall include polynucleotides encoding for the protein of interest, as modified for optimal expression in any given expression system, without regard to the overall sequence identity to SEQ ID NO: 1. Such designing can be effected with the aid of codon usage or preference tables such as are known in the art.

Figure 5:
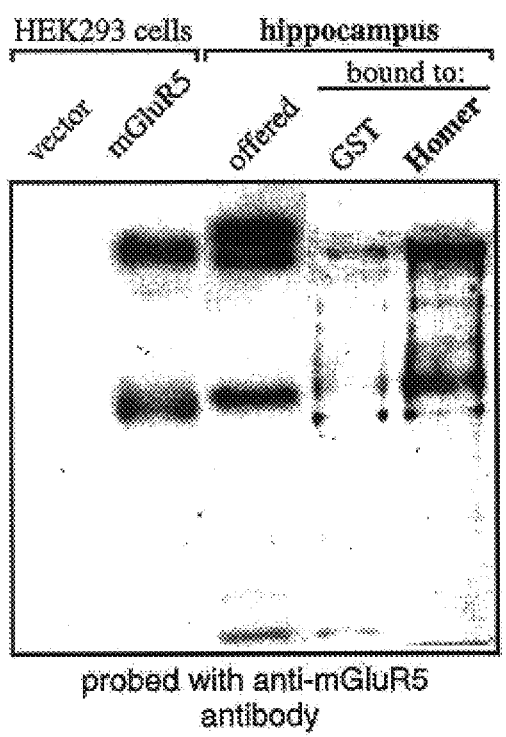
FIG. 5 shows a computer-generated image of an immunoblot of mGluR5 (140 kDa band) expressed in HEK-293 cells (lane 2) compared to cells transfected with vector alone (lane 1), of elution fractions from a GST affinity column (lane 4), and elution fractions of a GST-Homer affinity column (lane 5), where both columns were loaded with hippocampal extracts (lane 3), illustrating that the eluted Homer protein binds mGluR5.

As shown in FIG. 5, mGluR5 was expressed in HEK-293 cells (lane 2) and was compared to cells transfected with vector alone (lane 1). Here, mGluR5 migrates as a ~140 kDa major band with a secondary 50 kDa presumptive cleavage fragment. In extracts of hippocampus (lane 3), the upper (higher molecular weight) band appears as a doublet. In these experiments, hippocampal extracts were also passed over Affigel gel columns containing either GST or GST-Homer fusion protein and eluted with SDS loading buffer (lanes 4 and 5). Positive immunoblotting with anti-GluR5 antibody demonstrates the association of the rat Homer protein with the mGluR5 receptor in the extract.

b. Purification of Rat Homer Protein from Cell Extracts

The Homer protein and its analogs can be purified from a cell extracts using standard preparative procedures. Final stage purification may be carried out by any of a number of standard methods, including immunoaffinity column purification using antibodies raised against the Homer protein or fragments thereof, as described in Example 4.

3. Tissue Localization of Synaptic Activation Proteins

In experiments carried out in support of the present invention, it has been determined that expression of synaptic activation proteins is highly enriched in the central nervous system. For example, as demonstrated in the data shown in FIG. 3, rat Homer mRNA was found almost exclusively in the central nervous tissue.

Further, expression of Homer mRNA is strongly up-regulated in the hippocampus by seizure-induced neuronal activation. Peak mRNA expression occurs within 1 hour after seizure in the hippocampus (FIG. 3). The Homer protein is enriched in extracts of hippocampus and migrates as a doublet with an apparent molecular weight of 28/29 kDa (FIG. 3) that is rapidly induced by seizure.

Figure 4:
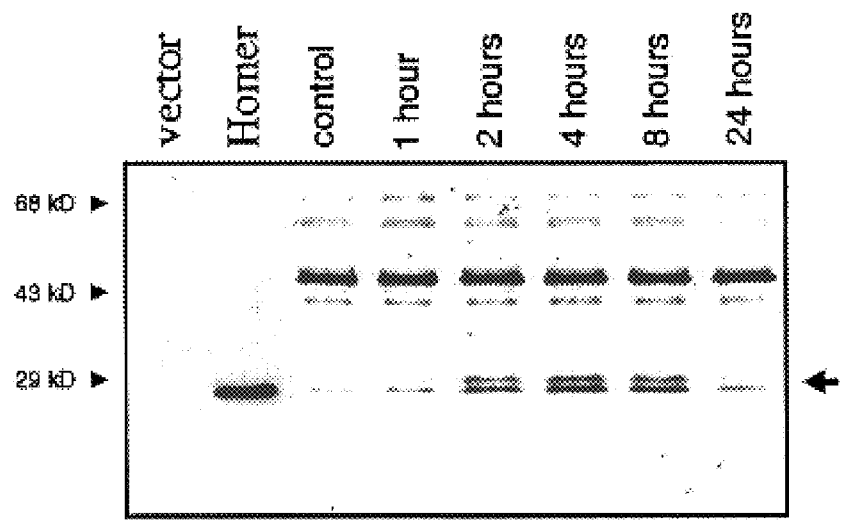
FIG. 4 shows a computer-generated image of an immunoblot analysis of the full-length binding proteins expressed in HEK-293 cells as a 28 kDa protein (lane "Homer") and as a 28/29 kDa doublet in hippocampus from seizure-stimulated rats, as indicated by the arrow.

Example 6 provides exemplary methods that can be used to measure expression levels of Homer protein. Anatomic and cellular patterns of rat Homer protein expression were examined by immunohistochemical analyses performed in adult rat brain. Consistent with its regulation as an IEG, Homer immunostaining in cortex markedly increased 4 hrs following a seizure (FIG. 4).

III. Cellular Binding Characteristics of Synaptic Activation Proteins

According to an important feature of the present invention, members of the synaptic activation protein family bind to specific central nervous system receptors or binding partners and modify the function of such proteins. As an example, and as discussed below, the rat Homer protein binds to two sub-types of metabotropic glutamate receptor (mGluR) found in the central nervous system—mGluR1α and mGluR5.

Additional central nervous system binding partners for specific synaptic activation binding proteins identified as discussed in Section II, above, can be identified using the methodologies described in Section A, below. Sections B and C describe methods used to characterize the interaction of a specific synaptic activation binding protein with its cellular binding partner(s).

1. Identification of Cellular Binding Sites for Synaptic Activation Proteins in the Central Nervous System Synaptic activation protein binding sites in central nervous tissue can be identified using a two-hybrid protein interaction assay (Ausubel, et al., 1992). This assay method provides a simple and sensitive means to detect the interaction between two proteins in living cells. Such an assay is described in Example 5, as it was used to identify certain of the functional binding partners for the rat Homer protein. Analogous assays are used to determine the cellular binding sites of the mouse and human proteins, and other homologous proteins according to the present invention.

The two-hybrid screening system is based on the observation that a protein-protein interaction can be detected if two potentially-interacting proteins are expressed as fusions, or chimeras. A first fusion protein contains one of a pair of interacting proteins fused to a DNA binding domain, and a second fusion protein contains the other of a pair of interacting proteins fused to a transcription activation domain. The two fusion proteins are independently expressed in the same cell, and interaction between the "interacting protein" portions of the fusions reconstitute the function of the transcription activation factor, which is detected by activation of transcription of a reporter gene. For use in the present invention, the first fusion protein contains the synaptic activation binding protein. The second fusion protein contains one of an expressed library of central nervous system specific proteins, as described below.

There are several possible configurations of the two-hybrid screening assay that can be used in the context of the present invention (Ausubel, et al., 1992). In one of these, a yeast GAL4 two hybrid system, protein-protein interactions are detected, based on reconstitution of function of GAL4, a transcriptional activator from yeast, by activation of a GAL1-lacZ reporter gene. Like several other transcription activating factors, GAL4 contains two distinct domains, a DNA binding domain and a transcription activation domain. Each domain can be independently expressed as a portion of a fusion protein composed of the domain, and a second, "bait" interacting protein. The two fusion proteins are then independently expressed together in a cell. When the two GAL4 domains are brought together by a binding interaction between the "bait" and the "binding" proteins, transcription of a reporter gene under the transcriptional control of GAL4 is initiated. The reporter gene typically has a promoter containing GAL4 protein binding sites (GAL upstream activating sequences, $UAS_G$). Exemplary reporter genes are the GAL1-lacZ, and GAL1-HIS3 reporter genes.

A second two hybrid system, described in detail by Ausubel, et al., (1992) utilizes a native E. coli LexA repressor protein, which binds tightly to appropriate operators. A plasmid is used to express one of a pair of interacting proteins (the "bait" protein, e.g., Homer protein) as a fusion to LexA. The plasmid expressing the LexA-fused bait protein is used to transform a reporter strain of yeast, such as EGY48, that contains pSH18-34.

In this strain, binding sites for LexA are located upstream of two reporter genes. In the first reporter system, the upstream activation sequences of the chromosomal LEU2 gene—required in the biosynthetic pathway for leucine (Leu)—are replaced in EGY48 with lexA operators, permitting selection for viability when cells are plated on medium lacking Leu. In the second reporter system, EGY48 harbors a plasmid, pSH18-34, that contains a lexA operator-lacZ fusion gene, permitting discrimination based on color when the yeast is grown on medium containing Xgal (Ausubel, et al., 1992).

The LexA library uses the inducible yeast GAL1 promoter to express proteins as fusions to an acidic domain ("acid blob") that functions as a portable transcriptional activation motif ("act"), and to other useful moieties. Expression of library-encoded proteins is induced by plating transformants on medium containing galactose (Gal), so yeast cells containing library proteins that do not interact specifically with the bait protein fail to grow in the absence of Leu. Yeast cells containing library proteins that interact with the bait protein form colonies within 2 to 5 days, and the colonies turn blue when the cells are streaked on medium containing Xgal. The plasmids are isolated and characterized by a series of tests to confirm specificity of the interaction with the initial bait protein. Those found to be specific are ready for further analysis (e.g., sequencing).

In experiments carried out in support of the present invention and described in Example 5 herein, the yeast GAL4 two-hybrid system was used to identify binding partners of the rat Homer protein in a rat brain cDNA library (Chevray and Nathans, 1992). A PCR product of the full-length Homer ORF with flanking SmaI sites was subcloned into the yeast expression vector pPC97. A random primed cDNA library was prepared from seizure stimulated adult rat hippocampus and cloned into the yeast expression vector pPC86. The library contains $2 \times 10^6$ independent cDNAs. A total of $1.5 \times 10^6$ clones were screened. Interacting proteins were identified by selection on plates lacking leucine, tryptophan, and histidine, restreaked and confirmed using a β-galactosidase assay.

One of the interacting cDNAs identified in this assay encodes the C-terminal 195 amino acids of mGluR5. This region of mGluR5 is cytosolic and has been implicated in phospholipase C (PLC)-mediated signaling in neurons. Confirmation and further characterization of binding was carried out as described in Section B, below.

2. Binding of Synaptic Activation Proteins to Cellular Components

In accordance with the discovery of the present invention, synaptic activation proteins bind cellular components, such as those identified according to the methods described in Section A, above. After determining the cellular binding partner candidate, the synaptic activation protein can be further tested for binding to the candidate in one or more of the in vitro binding assays such as those described below.

For example, the bacterially expressed GST-Homer fusion protein was tested for binding to native mGluR5 in detergent extracts of hippocampus in an in vitro binding assay as detailed in Example 7A. As shown in FIG. 5, mGluR5 binds to GST-Homer fusion protein, but not to GST alone.

Figure 6:
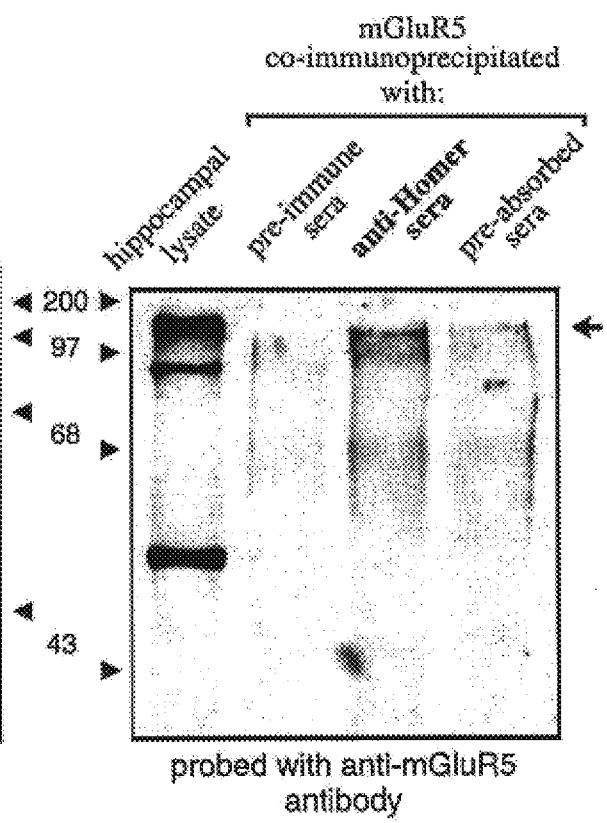
FIG. 6 shows a computer-generated image of an immunoblot showing immunoprecipitation of mGluR5 from hippocampal lysate (lane 1) by pre-immune serum (lane 2) anti-Homer protein antiserum (lane 3), and preabsorbed anti-Homer serum (lane 4), illustrating that Homer protein and mGluR5 interact in vivo.

Another method of assessing binding in vitro is provided by a co-immunoprecipitation assay, in which an antibody directed to one of the proteins is used to assess whether the two proteins form a binding complex in solution. FIG. 6 shows the results of assays testing co-immunoprecipitation of mGluR5 with Homer from hippocampus according to methods detailed in Example 7B. Here, extracts of hippocampus were immunoprecipitated with either pre-immune serum, anti-Homer serum or anti-Homer serum pretreated with GST-Homer. As shown, mGluR5 co-immunoprecipitates with Homer antiserum but not pre-immune serum. Additionally, co-immunoprecipitation was blocked by preadsorption of antisera with Homer antigen (lane 4), indicating the specificity of the antisera for the rat Homer protein.

Figure 7A:
FIGS. 7A and 7B show computer-generated images of immunostaining of rat parietal cortex tissue using anti-Homer antiserum (7A) and anti-mGluR5 antiserum (7B) at a magnification of 100×.
Figure 7B:
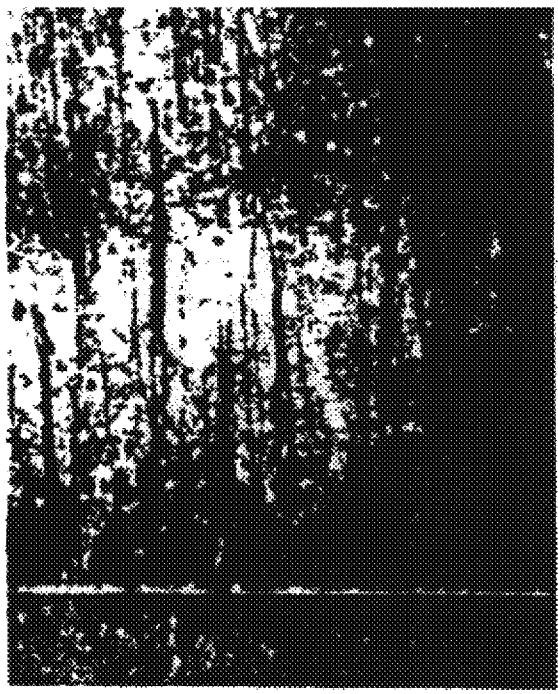

The potential for natural interaction between the synaptic activation protein and the candidate binding partner can be further assessed in situ and by immunostaining sections of brain tissue with antibodies directed to each of the proteins. The goal of this analysis is to establish that both proteins are expressed in the same regions of the cell. For example, FIGS. 7A and 7B show immunostaining of the rat Homer protein with anti-Homer antiserum (7A) and immunostaining of mGluR5 with anti-mGluR5 antibodies (7B) in adult rat parietal cortex. From these experiments, it is observed that mGluR5 and Homer immunostaining are both enriched in apical dendrites of Layer V pyramidal neurons. These data provide anatomic support for the interaction in vivo between the Homer protein and mGluR5.

Figure 7C:
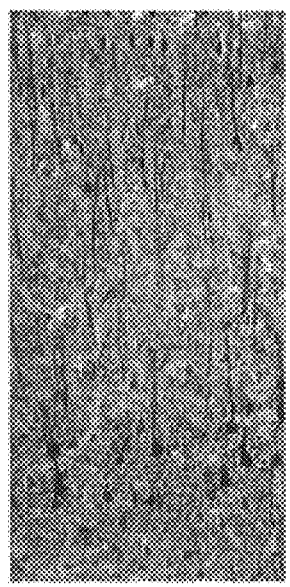
FIGS. 7C–7F show Homer protein immunoreactivity in the cortex of adult rats detected by peroxidase method control (C) and 4 hours after a seizure (D), where immunostaining is induced by seizure and is enriched in pyramidal neurons of layers II/III and V (mag. 100×); (E) illustrating that immunoreactivity is present along dendritic shafts (arrows) and in cell bodies but not in the nucleus (arrowhead; mag 600×); distal dendrites possess spine-like profiles (F, mag 1000×)
Figure 7D:
Figure 7E:
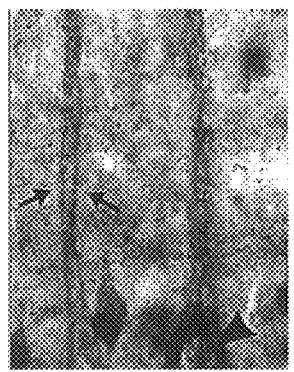
Figure 7F:
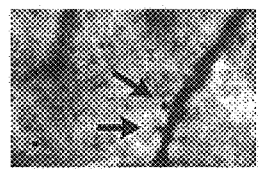
Figure 8A:
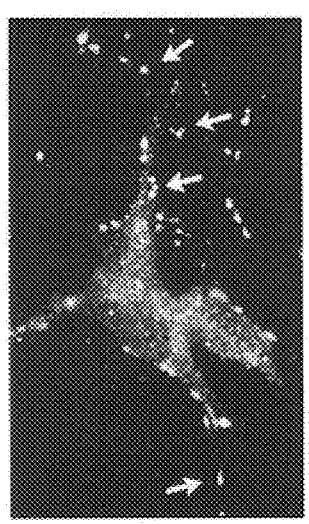
FIGS. 8A and 8B show double immunofluorescent localization of AMPA type glutamate receptor, GluR1 and Homer in neurons of primary hippocampal culture (mag 600×); where arrows indicate the punctate pattern of Homer staining that extensively colocalizes with GluR1, demonstrating that the Homer protein is targeted to excitatory synapses.
Figure 8B:
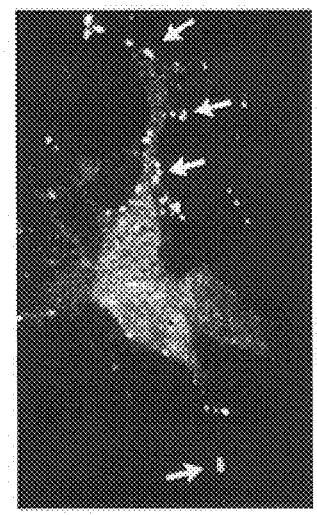

The anatomic and temporal pattern of Homer immunostaining precisely parallels its mRNA expression, as discussed in Section IV, below. Pyramidal neurons of cortical layers II/III and V showed the most intense immunostaining which typically filled the soma and extended into apical dendrites in a punctate pattern along the perimeter of the dendrite (FIG. 7C). Spine-like profiles were frequently seen in distal dendrites (FIG. 7D). Homer immunoreactivity was not present in the nucleus. The punctate pattern of Homer immunostaining was confirmed in primary cultures of hippocampal neurons (FIGS. 8A, 8B). Moreover, Homer extensively co-localized with immunostaining for the glutamate receptor GluR1 indicating that Homer is enriched at excitatory synapses. The anatomic pattern of Homer expression matches closely reports of mGluR5 immunoreactivity. mGluR5 immunoreactivity is enriched in dendrites of cortical pyramidal neurons, as well as many other neuronal populations that express Homer, and is present at excitatory synapses. The extensive co-distribution of Homer protein and mGluR5 in pyramidal neuron dendrites and excitatory synapses, together with the striking specificity of their physical interaction, support the notion that these proteins are physiological partners. The rat Homer protein is also highly expressed in Purkinje cells of the cerebellum. These cells strongly express mGluR1α, suggesting a physiological partnership between the two protein types in these neurons.

The studies described above with respect to the rat Homer protein are exemplary of the types of experiments which candidate synaptic activation protein family members may be subjected, in order to verify inclusion in the family. Upon identification of the particular binding partner protein to which the synaptic activation protein binds, appropriate functional assays are set up to determine whether such binding interferes with or enhances the biological function of the binding partner protein. For example, in the case of rat Homer protein, mGluR1 and mGluR5 are known to couple to phospholipase C and regulate phosphoinositide hydrolysis via phosphoinositidase C (PI-PLC), while mGluR2 and 4 negatively regulate adenylate cyclase (Nakanishi, 1994; Pin and Duvoisin, 1995). Therefore, in order to further determine whether rat Homer protein interferes with or enhances this functional activity, an assay is set up to monitor mGluR-dependent PI-PLC activity in the absence or presence of added rat Homer protein.

3. Peptide Sequence Specificity of Binding Interaction

According to a further feature of the present invention, it has been found that synaptic activation protein family members, exemplified by rat Homer protein, bind to specific peptide sequences. Such sequence specificity may be dictated by the PDZ domain, or by other domains present in the synaptic activation protein.

In studies carried out in support of the present invention, specificity of the interaction between the rat Homer protein and the metabotropic glutamate receptors mGluR5 and mGluR1α was examined using in vitro binding assays.

Metabotropic glutamate receptors uniquely possess long cytoplasmic C-terminal tails that are 67% identical over the last 55 amino acids and terminate in similar sequences; -RDYTQSSSSL and -RDYKQSSSTL, respectively (FIGS. 9A–9E). To measure the binding interaction, mGluR5 and mGluR1α were expressed in HEK-293 cells. Cell extracts were mixed with bead-linked GST-Homer and were then eluted with SDS loading buffer. Both transiently expressed full length mGluR1α and mGluR5 bind the rat Homer fusion protein, as shown in FIGS. 10A and 10D. When the C-terminal 4 amino acids of mGluR5 were deleted, binding of the mGluR5 to Homer was reduced by greater than 70% (FIG. 10D, lanes 3 and 4). Comparison of the C-terminal sequences of other metabotropic glutamate receptors indicates that mGluR2 and mGluR3 receptors share a similar C-terminal -TSSL (FIG. 8), although they diverge from mGluR1α and mGluR5 outside this region. Neither mGluR2 nor mGluR4 bind Homer protein (FIGS. 10B, 10C). An unrelated protein known to possess the C-terminal TSSL (RSK1) was also tested for binding, but this protein did not bind Homer. Based on these data, it is believed that the final 4 amino acids are important, but not sufficient for binding.

The foregoing data indicate that the Homer protein specifically interacts with PI-PLC linked metabotropic glutamate receptors, and that the binding specificity is determined, at least in part, by the C-terminal 4 amino acids of these receptors. Specific binding sites for additional synaptic activation proteins may have similar or divergent amino acid sequences that can be empirically determined, using methods similar to those discussed above.

The effect of deletion mutations of the Homer protein on its binding to mGluR5 was examined by measuring binding of the full length Homer-GST fusion protein to myc-tagged mGluR5 C-terminal 195 aa fragment expressed from HEK-293 cells. Similarly, deletion constructs lacking the C-terminal 55 amino acids also bound mGluR5. By contrast, deletion of the N-terminal 108 amino acids of the Homer protein, which includes the GLGF sequence, abolished binding to mGluR5. These observations indicate a role for the GLGF region in binding to the C-terminal sequence of mGluR5.

IV. In Vivo Regulation of Expression

It is a discovery of the present invention that synaptic activation proteins belonging to the family exemplified by the rat Homer protein may be dynamically regulated by neuronal activity, including seizure activity and acute cocaine administration, as discussed above. In addition, experiments carried out in support of the present invention show that the rat Homer protein is developmentally regulated with peak expression in the rat forebrain from the third to fifth postnatal weeks (FIG. 11). During this period of peak developmental expression, Homer protein mRNA is markedly induced in cerebral cortex of dark-reared rats within 30 min. of the first visual experience (FIGS. 12A–12F). Moreover, monocular deprivation, by blockade of retinal activity with tetrodotoxin, causes a rapid reduction of Homer mRNA in the contralateral visual cortex (FIG. 13). These observations indicate that developmental expression of the synaptic activation protein Homer is regulated in the cortex by natural synaptic activity. It is anticipated that additional members of the synaptic activation protein family may share these, or very similar, expression characteristics.

In the adult, Homer mRNA is rapidly induced in the hippocampus of awake, behaving rats by NMDA-dependent synaptic stimuli that induce long-term potentiation (FIG. 14). The most prominent induction occurs in hippocampal granule cell neurons and is similar in magnitude to induction by seizure. The Homer protein is also rapidly induced in the striatum by cocaine (FIG. 15) suggesting regulation by dopamine receptor mechanisms. These studies indicate that, unlike other known PDZ proteins, the Homer protein is rapidly regulated by multiple forms of physiological neuronal activity.

The many novel features of the rat Homer protein suggest an important role in glutamatergic synaptic plasticity for Homer and its human analog.

V. Utility

The polynucleotide and polypeptide compositions that form a part of the present invention have utility as major components of diagnostic assays and screening assays for identifying drugs capable of enhancing or inhibiting the interaction between synaptic activation proteins and their cellular binding sites. Specific examples of such assays and how they can be used are provided in the sections that follow.

1. Screening Assays

The synaptic activation proteins described herein may be used in screening assays to identify compounds that interfere with or modulate binding of the protein Homer to mGluR5 or mGluR1α, and hence with PI-linked mGluR activity. In accordance with the present invention, compounds identified by this screening assay may be used as drugs for treating epilepsy, abnormal brain development, neural injury, trauma and certain chemical addictions.

Assay formats for measuring the protein-protein interaction are known in the art. For example, purified synaptic activation protein can be coated onto a solid phase, such as a microtiter plate, followed by blocking of open plate binding sites, according to standard methods. mGluR is then added to the plate in the absence or presence of a test compound. Detection of mGluR bound to synaptic activation protein is accomplished by direct labeling of the mGluR or by subsequent addition of a labeled, mGluR-specific binding reagent, such as an antibody. The binding reagent may be radiolabeled, e.g., with $^{125}I$, or may be labeled with a fluorescent dye, an enzyme capable of generating a signal (e.g., horseradish peroxidase), gold or biotin according to methods well know in the art (Howard, 1993). Detection of binding is then carried out using methods appropriate to the signal generated. A test compound is selected for drug development if it significantly alters binding between the proteins.

Accordingly, polynucleotides forming part of the present invention can be used in the large-scale production of synaptic activation proteins for the above-described screening assays.

2. Diagnostic Assays

Using the interaction between the rat or human form of the synaptic activation Homer protein with mGluR5 as an example, a diagnostic assay test kit can be made for measuring induction of the synaptic activation protein. It is appreciated that induction of synaptic activation protein may serve as a measure of brain activation, such as seizure activity in central nervous tissue. Here, measurement of synaptic activation protein levels may serve as an indicator of the level of seizure activity and/or neuronal damage consequent to such activity. Such measurement may also serve as an indicator of the level of acute cocaine intoxication (c.f., Section IV, above).

Diagnostic kits for measuring levels of synaptic activation protein can take the form of a radioimmunoassay, where sample protein levels are measured by displacement of labeled control protein from a specific antibody. Alternatively, protein levels can be measured in an ELISA sandwich style assay, where a monoclonal antibody directed to a specific epitope of the synaptic activation protein is attached to the solid phase. Test sample is then added, followed by detectable monoclonal antibody, directed to a different epitope of the synaptic activation protein. Detectable signal is proportional to amount of synaptic activation protein present in the sample.

The following examples illustrate, but in no way are intended to limit the present invention.

EXAMPLE 1

Cloning of Synaptic Activation Protein Homer by Differential Screening

Superinduction of IEBs in the hippocampus was achieved by pretreating rats with cycloheximide and 15 minutes later repeatedly administer maximal electroconvulsive seizures (MECS), for a total of 12 MECS over a time period of 3 hours.

Total RNA was isolated from hippocampus of rats treated with MECS and cycloheximide. Poly(A)$^+$ RNA was selected by oligo dT column chromatography. The RNA was then converted to cDNA using an oligo dT/XhoI primer and directionally cloned into λ Zap II (Stratagene, La Jolla, Calif.) according to manufacturer's protocol. The complexity of this library was ~2×10$^6$ independent clones. This stimulated parent library was then used to prepare a subtracted library enriched for genes induced in hippocampus following seizure. The stimulated library was plated at a density of 50000 pfu/dish (40 dishes total) and phage DNA was prepared. This DNA was linearized at the 3' end of the cDNA insert using XhoI and then used as template in the presence of T3 RNA Polymerase to synthesize large amounts of "in vitro" cRNA. In order to remove incomplete transcripts and vector sequences, Poly(A)$^+$ cRNA was isolated from the cRNA by oligo dT column chromatography. The cRNA was converted to cDNA using an oligo dT/XhoI primer and superscript reverse transcriptase (Gibco BRL, Ground Island, N.Y.). The RNA template was removed by base denaturation followed by column chromatography on "SEPHADEX G-50" (Pharmacia, Piscataway, N.J.) and this cDNA was subtracted against Poly(A)$^+$ RNA isolated from normal adult rat brain. For subtraction the brain "driver" Poly(A)$^+$ RNA was biotinylated using "PHOTOPROBE" (long arm) biotin (Vector Laboratories, Inc., Burlingame, Calif.). For the first round of subtraction a 20-fold excess of biotinylated driver brain RNA (200 ug) was hybridized with the stimulated cDNA (10 ug) for 48 hours at 68° C. Non-differential cDNA/bioRNA hybrids were removed by the addition of streptavidin (Vector Laboratories, Inc., Burlingame, Calif.) followed by phenol extraction and single stranded cDNA was recovered in the aqueous phase. The first round of subtraction removed 80% of the starting cDNA and the remaining single stranded cDNA was hybridized for an additional 48 hours at 68° C. with a 100-fold excess of biotinylated driver liver RNA (200 ug). This second round of subtraction removed an additional 16% of the starting stimulated cDNA. The remaining material was size fractionated by column chromatography on "SEPHADEX G-50" (Pharmacia, Piscataway, N.J.) to remove degraded and small cDNAs. The "stimulated" subtracted single stranded cDNA was converted to double stranded using "SEQUENASE" DNA Polymerase (USB) and the SK primer (Stratagene, La Jolla, Calif.). Following digestion with EcoRI and XhoI, and size fractionation by column chromatography, the subtracted cDNA was directionally cloned into λ ZAPII (subtracted/MECS and cycloheximide/hippocampus). The complexity of this subtracted cDNA library was ~5×10$^6$ independent clones. This phage library was then plated at a density of ~1000 phage/15 cm dish and replicate lifts were obtained. Lifts were then hybridized with $^{32}$P-dCTP radiolabelled cDNA prepared from poly A$^+$ RNA of hippocampus from either naive control rats or rats that received MECS/cycloheximide stimulation. Single stranded cDNA was prepared using "SUPERSCRIPT" according to manufacturer's instructions. Following base denaturation of the RNA template the cDNA was radiolabelled to a specific activity of 4×10$^9$ cpm/ug by the random priming method. Filters were hybridized for 2 days at 65° C. with the subtracted cDNA probe and then washed with 0.5×SSC/0.2% SDS at 65° C. and exposed to X-ray film at −80° C. with intensifying screens.

EXAMPLE 2

Preparation of Homer Protein Oligonucleotides and Vectors

A mammalian expression construct of full length Homer was prepared by cloning the 5' EcoRI fragment (1.6 kb) into pRK5 (Genentech, South San Francisco, Calif.), according to methods known in the art (Ausubel).

EXAMPLE 3

Synthesis of Homer Protein

Homer protein was expressed in human embryonic kidney cells (IDEK293). The Homer eukaryotic expression vector (sRK5 Homer) was transfected into HEK-293 cells by standard calcium phosphate precipitate method. Cells were harvested 24–48 hours after transfection.

1. Cell-free Translation

Homer protein has been expressed using several strategies. Homer was first expressed from the cDNA cloned in pBSKS- (Stratagene, La Jolla, Calif.) using T3 polymerase and the in vitro transcription and translation method according to manufacturer's instructions (Promega Biotech, Madison, Wis.). This technique was used to assess the size of Homer (Homer migrates on SDS-PAGE with an apparent molecular mass of 28 kDa), confirming the size predicted by the ORF. This method can also be used to prepare Homer protein for other uses described herein.

2. Cellular Expression

Bacterial fusion proteins of Homer were prepared by cloning the ORF into pTrkHis (InVitrogen, San Diego, Calif.) and pGEX (Phamacia, Piscataway, N.J.). Fusion proteins were expressed in bacteria and purified over the appropriate affinity column according to manufacturers' instructions.

Homer was expressed in eukaryotic cells (human embryonic kidney cells, American Type Culture Collection, Rockville, Md.) by cloning a 2 kB EcoRI restriction fragment that included the ORF into the vector pRK5 (Genentech, South San Francisco, Calif.), according to standard procedures known in the art. The eukaryotic expression vector (pRK4 Homer) was transfected into HEK-293 cells by standard calcium phosphate precipitate methods. Cells were harvested 24–48 hours after transfection. The proteins isolated from these cells were used in binding assays and to confirm the size of the native protein.

Homer was also expressed yeast. The ORF was cloned into pPC86 (Chevray and Nathans, 1992) and used to screen for proteins that interact with Homer. This screen first determined that Homer interacts with the type 5 metabotropic glutamate receptor.

EXAMPLE 4

Immunoaffinity Purification of Homer Protein

Monoclonal antibodies are coupled to protein A or G (depending upon Ig isotype) beads (commercially available from Pharmacia, Piscataway, N.J.) according to manufacturer's instructions and the bead complexes are collected in an immunoaffinity column. Cleared whole cell lysates are preabsorbed to agarose beads, passed through the immunoaffinity column, washed with several volumes of wash buffer, then the protein of interest is eluted from the column using a predetermined buffer condition. Commonly, high salt conditions are used for such elution.

Alternatively, antibodies may be directly attached to a chromatography solid phase reagent, such as "SEPHAROSE 4B-200" (Pharmacia, Piscataway, N.J.) according to methods known in the art (Garvey, et al., 1977).

EXAMPLE 5

Two-hybrid Protein Binding Assay

The full-length Homer ORF with flanking SmaI sites was subcloned into the yeast expression vector pPC97. A random primed cDNA library was prepared from seizure stimulated adult rat hippocampus and cloned into the yeast expression vector pPC86. The library contains 6×10$^6$ independent cDNAs and a total of 1.5×10$^6$ were screened. Interacting proteins were identified by colony selection on plates lacking leucine, tryptophan, and histidine and confirmed using a β-galactosidase assay (Ausubel, et al., 1992). Alternatively, a commercially available 2-hybrid detection system can be used to detect protein-protein interactions, e.g., "HYBRID HUNTER" (InVitrogen, San Diego, Calif.).

EXAMPLE 6

Measurement of Expression Levels

1. Antisera Preparation

Rabbit polyclonal antiserum for the mGluR receptors were generated against C-terminal peptides; mGluR1 as reported previously, mGluR2/3 (Chemicon International Inc.), mGluR4 (Wyeth-Ayerst Research, Princeton, N.J.), and mGluR5 against a C-terminal 21 aa peptide. Anti-Homer rabbit polyclonal antisera were generated using either the full length Homer ORF as a GST fusion or a C-terminal 18 aa peptide. Both antisera detected a 28 kDa protein when Homer was expressed in HEK-293 cells and a seizure-inducible 28/29 kDa doublet protein in hippocampus.

2. Immunoblot Analysis

Protein mixtures were separated by SDS-PAGE according to standard methods. After electrophoresis the gel was washed extensively, and the proteins were then transferred to nitrocellulose according to methods known in the art (Ausubel, et al., 1992). The nitrocellulose was then incubated with polyclonal anti-mGluR5 rabbit polyclonal antiserum diluted according to pre-determined detection criteria. The blot was washed, then incubated with radiolabeled or enzyme-linked anti-rabbit antiserum. Dried gels were subjected to autoradiography.

EXAMPLE 7

Binding of Synaptic Activation Protein Homer Protein to mGluR5

1. Binding of Bacterially-Expressed GST-Homer Fusion Protein in Bacterial Extracts Hippocampal lysate was prepared by sonicating hippocampi of 21 day old rats (3×10 seconds) in PBS and 1% Triton with protease inhibitors, centrifuging for 10 minutes at 15,000 g, and preclearing with CL-4B sepharose beads (Pharmacia, Piscataway, N.J.). Homer affinity columns were prepared by irreversibly crosslinking Homer GST fusion protein to Affigel agarose beads (1 mg Homer protein per 1 ml bed volume; Bio-Rad Laboratories, Richmond, Calif.). 40 ml of beads were then incubated with lysate from one hippocampus for one hour at 4° C., washed three times with PBS, and bound mGluR5 was eluted by boiling in 3×loading buffer.

2. Binding of Rat Homer Protein to Metabotropic Glutamate Receptors

For experiments examining specificity of Homer binding to metabotropic glutamate receptors, HEK-293 cells were transiently transfected with mGluR1α, mGluR2, mGluR4 or mGluR5 expression constructs, scraped into PBS+1% Triton X100, sonicated 2×10 seconds, centrifuged at 15,000 g for 10 minutes at 4° C., and pre-cleared. Lysate from half of a 10 cm plate was incubated with 50 μl of beads linked to 250 ng of protein and washed as above. Samples were analyzed by western blot analysis using the appropriate polyclonal mGluR antibody. Deletion constructs of Homer were prepared by PCR and cloned as fusion constructs with GST in pGEX (Pharmacia, Piscataway, N.J.).

C. Co-Immunoprecipitation of Homer Protein and mGluR5

Hippocampal lysate was prepared as above. Rabbit anti-Homer serum or pre-immune serum were irreversibly linked to "AFFIGEL" agarose beads (Bio-Rad Laboratories, Richmond, Calif.) and washed extensively with PBS. 50 μl beads were incubated with lysate from one hippocampus overnight at 4° C., washed 2× with PBS with 1% Triton and 2×with PBS, resuspended in 3× SDS loading buffer and analyzed by gel electrophoresis and western blot analysis. In control experiments, coimmunoprecipitation of mGluR5 was blocked by pre-incubating anti-Homer linked beads with 50 μg of Homer GST-fusion protein for 1 hour at 4° C.

EXAMPLE 8

Immunohistochemistry

Six week old rats were anesthetized and perfused with 4% paraformaldehyde. Whole brains were removed and placed in the fixative for one hour and then into 30% Sucrose for 72 hours. 35 μm sections were cut using a sliding microtome, blocked and permeabilized for one hour in 1% dry milk and 5% normal goat serum in PBS with 0.1% Triton. Sections were incubated in primary antibody for 24 hours, washed and immunoperoxidase staining was performed with a Vectastain Elite ABC Kit (Vector Laboratories, Inc., Burlingame, Calif.). Elimination of the primary or preadsorption of Homer or mGluR5 antisera with the immunogenic peptides completely blocked staining. Primary hippocampal cultures were prepared from 4 day postnatal rat pups. GluR1 staining was performed using Cy3 labeled FAB fragment of an antibody raised against synthetic peptide corresponding to amino acids 251–269. Cells were fixed in 4% paraformaldehyde for 1 hr. permeabilized with 0.1% Triton and incubated with affinity purified anti-Homer antiserum for overnight at 4° C. Homer was detected by FITC coupled goat anti-rabbit antibody (Vector Laboratories, Inc., Burlingame, Calif.).

EXAMPLE 9

Assay Kits

A. Preparation of Monoclonal Antibodies

Balb/c mice are anesthetized by pentobarbital injection. After shaving the fur from the splenic area, the area is swabbed with 70% ethanol and draped with sterile gauze soaked in sterile isotonic saline. A cutaneous incision about 1 cm in length is made in the left midcapsular line, followed by incision of the abdominal way and peritoneum. Using forceps, a nitrocellulose disc, excised from a nitrocellulose blot of a gel containing separated Homer protein, is inserted into the spleen through the slit and carefully moved distally toward the caudal end until the disc is completely embedded in the splenic tissue. Alternatively, extracted protein is injected intrasplenically in a volume of less than 5 microliters, or intraperitoneally, according to standard methods. The spleen is observed to ensure that bleeding is not excessive, and returned to the peritoneal cavity. The abdominal wall and the skin are sutured separately with interrupted 4-0 silk sutures. Eight to ten days later the mice are bled and the serum tested for antibody titer against molecular weight matched proteins fractionated by preparative SDS electrophoresis (western blot). If the antibody titer is low, the procedure is repeated.

Then, an antibody producing hybridoma is produced using standard protocols. For example, p3×63-Ag8.653 myeloma cells originating from Balb/c mice (nonsecreting myeloma, 8-azaguanine-resistant, HPRT) are fused according to standard PEG4000 (Merck, Philadelphia, Pa.) fusion protocol with immunized splenocytes at a myeloma:lymphocyte ratio of 10:1 and the cells are plated in microplates in medium containing HAT, and 10% conditioned medium from J774.1 murine macrophage line pulsed with LPS.

Relevant polypeptides separated by preparative SDS-PAGE and eluted therefrom are used to check the specificity of the generated monoclonal antibodies. Usually, eluate containing 30 to 80 μg/ml of partially purified protein are applied to microtiter wells and incubated, for example, for 2 hours at 37° C. followed by 2 hours at 4° C. After washing, supernatant from each hybridoma well is added and incubated for 1 hour at 4° C., then washed several times with PBS. Fluoresceinated goat-anti-mouse immunoglobulin "second" antibody is added, then washed, and binding is monitored by fluorometry.

Positive hybridoma clones are expanded, re-cloned, and injected into Pristane-treated Balb/c mice for large-scale production of antibody (ascites). Antibody from the ascites fluid are purified on Protein A or G (according to the Ig isotype) columns.

B. Solid Phase Immunoassay

Purified rat Homer is diluted in a standard coating dilution buffer, such as phosphate-buffered saline (PBS) and coated onto a solid phase, such as a microtiter plate, followed by blocking of open plate binding sites with an unrelated protein such as bovine serum albumin or casein, according to standard methods. mGluR is then added to the plate in the absence or presence of a test compound. Detection of mGluR bound to synaptic activation protein is accomplished by direct labeling of the mGluR or by subsequent addition of a labeled, mGluR-specific binding reagent, such as a monoclonal or polyclonal antibody specific for mGluR. A test compound is selected for drug development if it significantly alters binding between the proteins.

While the invention has been described with reference to specific methods and embodiments, it will be appreciated that various modifications and changes may be made without departing from the invention.

It is claimed:

1. An isolated polynucleotide encoding a polypeptide having at least 70% sequence identity to the sequence SEQ ID NO:2.

2. The isolated polynucleotide of claim 1, wherein said sequence identity is at least about 80%.

3. The isolated polynucleotide of claim 1, wherein said polynucleotide has the sequence as set forth in SEQ ID NO:1.

4. A vector which contains a polynucleotide encoding a polypeptide having a least about 80% sequence identity to the sequence SEQ ID NO:2.

5. The vector of claim 4, wherein said polynucleotide has the sequence as set forth in SEQ ID NO:1.

6. An isolated polynucleotide selected from the group consisting of:
   a) SEQ ID NO:1;
   b) SEQ ID NO:1, wherein T is U;
   c) sequences complementary to a) or b);
   d) degenerate variants of SEQ ID NO:1;
   e) nucleic acid sequences that have at least about 70% sequence identity to the nucleic acid sequence of SEQ ID NO:1 and;
   f) nucleic acid sequences that encode a polypeptide having at least about 80% sequence identity to the amino acid sequence of SEQ ID NO:2.

7. A vector containing a polynucleotide of claim 6.

8. The vector of claim 7, wherein the vector is a plasmid vector.

9. A host cell comprising a vector of claim 7.

10. The host of claim 9, wherein the cell is a prokaryotic cell.

11. The host of claim 9, wherein the cell is a eukaryotic cell.

12. A method for producing a polypeptide as set forth in SEQ ID NO:2 comprising:
   a) culturing a host cell of claim 9, under conditions that allow expression of the polypeptide; and
   b) producing the polypeptide as set forth in SEQ ID NO:2.

13. The method of claim 12, further comprising isolating the polypeptide.

14. The vector of claim 7, wherein the vector is a viral vector.

* * * * *

SEQUENCE LISTING

<160> NUMBER OF SEQ ID NOS: 9

<210> SEQ ID NO 1
<211> LENGTH: 558
<212> TYPE: DNA
<213> ORGANISM: Rattus sp.
<220> FEATURE:
<221> NAME/KEY: CDS
<222> LOCATION: (1)..(558)

<400> SEQUENCE: 1

```
atg ggg gaa caa cct atc ttc agc act cga gct cat gtc ttc cag atc         48
Met Gly Glu Gln Pro Ile Phe Ser Thr Arg Ala His Val Phe Gln Ile
  1               5                  10                  15 gac cca aac aca aag aag aac tgg gta ccc acc agc aag cat gca gtt         96
Asp Pro Asn Thr Lys Lys Asn Trp Val Pro Thr Ser Lys His Ala Val
             20                  25                  30 act gtg tct tat ttc tat gac agc aca agg aat gtg tat agg ata atc        144
Thr Val Ser Tyr Phe Tyr Asp Ser Thr Arg Asn Val Tyr Arg Ile Ile
         35                  40                  45 agt cta gac ggc tca aag gca ata ata aat agc acc atc act cca aac        192
Ser Leu Asp Gly Ser Lys Ala Ile Ile Asn Ser Thr Ile Thr Pro Asn
     50                  55                  60 atg aca ttt act aaa aca tct caa aag ttt ggc caa tgg gct gat agc        240
Met Thr Phe Thr Lys Thr Ser Gln Lys Phe Gly Gln Trp Ala Asp Ser
 65                  70                  75                  80 cgg gca aac act gtt tat gga ctg gga ttc tcc tct gag cat cat ctc        288
Arg Ala Asn Thr Val Tyr Gly Leu Gly Phe Ser Ser Glu His His Leu
                 85                  90                  95 tca aaa ttt gca gaa aag ttt cag gaa ttt aaa gaa gct gct cgg ctg        336
Ser Lys Phe Ala Glu Lys Phe Gln Glu Phe Lys Glu Ala Ala Arg Leu
            100                 105                 110 gca aag gag aag tcg cag gag aag atg gaa ctg acc agt acc cct tca        384
Ala Lys Glu Lys Ser Gln Glu Lys Met Glu Leu Thr Ser Thr Pro Ser
        115                 120                 125 cag gaa tca gca gga gga gat ctt cag tct cct tta aca cca gaa agt        432
Gln Glu Ser Ala Gly Gly Asp Leu Gln Ser Pro Leu Thr Pro Glu Ser
    130                 135                 140 atc aat ggg aca gat gat gag aga aca ccc gat gtg aca cag aac tca        480
Ile Asn Gly Thr Asp Asp Glu Arg Thr Pro Asp Val Thr Gln Asn Ser
145                 150                 155                 160 gag cca agg gct gag cca gct cag aat gca ttg cca ttt tca cat agg        528
Glu Pro Arg Ala Glu Pro Ala Gln Asn Ala Leu Pro Phe Ser His Arg
                165                 170                 175 tac aca ttc aat tca gca atc atg att aaa                                 558
Tyr Thr Phe Asn Ser Ala Ile Met Ile Lys
                180                 185
```

```
<210> SEQ ID NO 2
<211> LENGTH: 186
<212> TYPE: PRT
<213> ORGANISM: Rattus sp.

<400> SEQUENCE: 2

Met Gly Glu Gln Pro Ile Phe Ser Thr Arg Ala His Val Phe Gln Ile
 1               5                  10                  15

Asp Pro Asn Thr Lys Lys Asn Trp Val Pro Thr Ser Lys His Ala Val
            20                  25                  30

Thr Val Ser Tyr Phe Tyr Asp Ser Thr Arg Asn Val Tyr Arg Ile Ile
        35                  40                  45

Ser Leu Asp Gly Ser Lys Ala Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Glu His His Leu
                85                  90                  95

Ser Lys Phe Ala Glu Lys Phe Gln Glu Phe Lys Glu Ala Ala Arg Leu
           100                 105                 110

Ala Lys Glu Lys Ser Gln Glu Lys Met Glu Leu Thr Ser Thr Pro Ser
       115                 120                 125

Gln Glu Ser Ala Gly Gly Asp Leu Gln Ser Pro Leu Thr Pro Glu Ser
   130                 135                 140

Ile Asn Gly Thr Asp Asp Glu Arg Thr Pro Asp Val Thr Gln Asn Ser
145                 150                 155                 160

Glu Pro Arg Ala Glu Pro Ala Gln Asn Ala Leu Pro Phe Ser His Arg
                165                 170                 175

Tyr Thr Phe Asn Ser Ala Ile Met Ile Lys
            180                 185

<210> SEQ ID NO 3
<211> LENGTH: 49
<212> TYPE: PRT
<213> ORGANISM: Homo sapiens

<400> SEQUENCE: 3

Met Gly Glu Gln Pro Ile Phe Ser Thr Arg Ala His Val Phe Gln Ile
 1               5                  10                  15

Asp Pro Asn Thr Lys Lys Asn Trp Val Pro Thr Ser Lys His Gly His
            20                  25                  30

Arg Phe Tyr Phe Tyr Asp Val Thr Arg Asn Ser Tyr Arg Ile Ile Ser
        35                  40                  45

Val

<210> SEQ ID NO 4
<211> LENGTH: 153
<212> TYPE: PRT
<213> ORGANISM: Mus sp.

<400> SEQUENCE: 4

Tyr Phe Tyr Asp Val Thr Arg Asn Ser Tyr Arg Ile Ile Ser Val Asp
 1               5                  10                  15

Gly Ala Lys Val Ile Ile Asn Ser Thr Ile Thr Pro Asn Met Thr Phe
            20                  25                  30

Thr Lys Thr Ser Gln Lys Phe Gly Gln Trp Ala Asp Ser Arg Ala Asn
        35                  40                  45
```

-continued

```
Thr Val Phe Gly Leu Gly Phe Ser Ser Glu Leu Gln Leu Thr Lys Phe
            50                  55                  60

Ala Glu Lys Phe Gln Glu Val Arg Glu Ala Ala Arg Leu Ala Arg Asp
 65                  70                  75                  80

Lys Ser Gln Glu Lys Thr Glu Thr Ser Ser Asn His Ser Gln Glu Ser
                 85                  90                  95

Gly Cys Glu Thr Pro Ser Ser Thr Gln Ala Ser Ser Val Asn Gly Thr
                100                 105                 110

Asp Asp Glu Arg Ala Ser His Ala Ser Pro Ala Asp Thr His Leu Arg
            115                 120                 125

Ser Glu Asn Asp Arg Leu Lys Ile Ala Leu Thr Gln Ser Ala Ala Asn
        130                 135                 140

Val Lys Lys Trp Glu Met Glu Leu Gln
145                 150

<210> SEQ ID NO 5
<211> LENGTH: 10
<212> TYPE: PRT
<213> ORGANISM: Rattus sp.

<400> SEQUENCE: 5

Arg Asp Tyr Lys Gln Ser Ser Ser Thr Leu
 1               5                  10

<210> SEQ ID NO 6
<211> LENGTH: 10
<212> TYPE: PRT
<213> ORGANISM: Rattus sp.

<400> SEQUENCE: 6

Glu Val Val Asp Ser Thr Thr Ser Ser Leu
 1               5                  10

<210> SEQ ID NO 7
<211> LENGTH: 10
<212> TYPE: PRT
<213> ORGANISM: Rattus sp.

<400> SEQUENCE: 7

Glu Val Leu Asp Ser Thr Thr Ser Ser Leu
 1               5                  10

<210> SEQ ID NO 8
<211> LENGTH: 10
<212> TYPE: PRT
<213> ORGANISM: Rattus sp.

<400> SEQUENCE: 8

Thr Tyr Val Thr Tyr Thr Asn His Ala Ile
 1               5                  10

<210> SEQ ID NO 9
<211> LENGTH: 10
<212> TYPE: PRT
<213> ORGANISM: Rattus sp.

<400> SEQUENCE: 9

Arg Asp Tyr Thr Gln Ser Ser Ser Ser Leu
 1               5                  10
```